Figure 1:
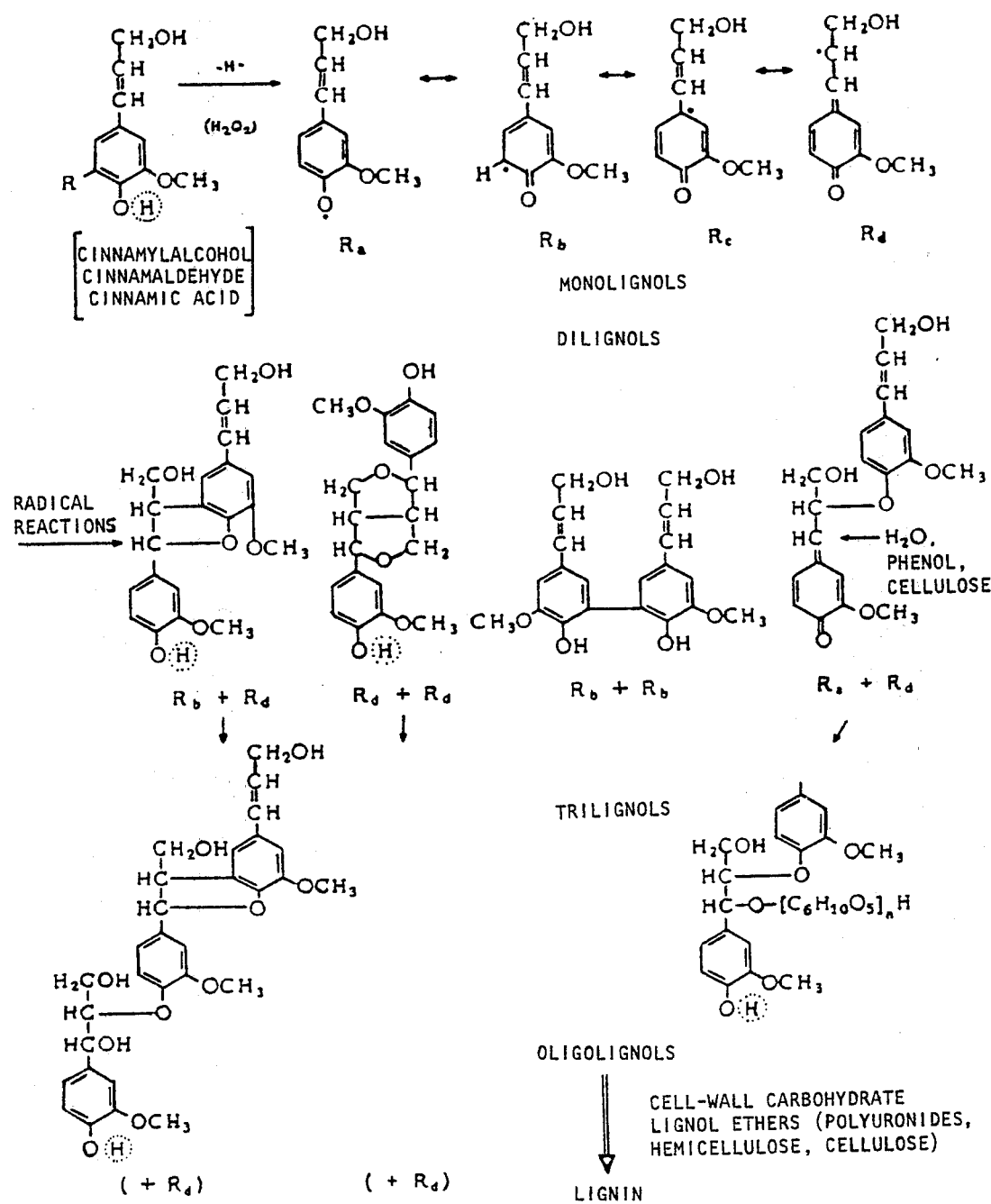

United States Patent [19]

Haars et al.

[11] 4,432,921
[45] Feb. 21, 1984

[54] PROCESS FOR PRODUCING A BINDER FOR WOOD MATERIALS

[75] Inventors: Annegret Haars; Aloys Hüttermann, both of Göttingen, Fed. Rep. of Germany

[73] Assignee: Gesellschaft für Biotechnologische Forschung, Braunschweig, Fed. Rep. of Germany

[21] Appl. No.: 309,174

[22] Filed: Oct. 7, 1981

[30] Foreign Application Priority Data

Oct. 8, 1980 [DE] Fed. Rep. of Germany ....... 3037992

[51] Int. Cl.³ .............................................. B29J 5/00
[52] U.S. Cl. .................................... 264/109; 436/156
[58] Field of Search ......................... 264/109; 436/156

[56] References Cited

U.S. PATENT DOCUMENTS 4,183,997 1/1980 Stofko ................................ 264/109
4,194,997 3/1980 Edler .................................. 264/109

FOREIGN PATENT DOCUMENTS 2406887 8/1975 Fed. Rep. of Germany.

Primary Examiner—James R. Hall
Attorney, Agent, or Firm—Max Fogiel

[57] ABSTRACT

A process in which phenolic substances, particularly lignin sulfonate, are used to produce a binder for wood materials. The phenolic substance is activated by displacing it with enzymes. Phenolic groups of the phenolic substance become oxidatively polymerized by a radical mechanism, so that the phenolic substance is changed into an active binder.

6 Claims, 4 Drawing Figures

MOLECULAR WEIGHT OF UNTREATED LIGNIN SULFONATE.

MOLECULAR WEIGHT OF UNTREATED LIGNIN SULFONATE.

FIG. 3

MOLECULAR WEIGHT OF LIGNIN SULFONATE TREATED IN ACCORDANCE WITH THE INVENTION (AS DETERMINED BY GELCHROMATOGRAPHY AN SEPHAROSE CL 6B).

A) LIGNIN SULFONATE FROM A GLUCOSE AND LIGNIN-SULFONATE CULTURE AFTER 19 DAYS OF INCUBATION, $M_n = 1.2 \times 10^6$. $M_w = 1.5 \times 10^6$.

B) LIGNIN SULFONATE FROM A CELLOBIOSE AND LIGNIN-SULFONATE CULTURE AFTER 19 DAYS OF INCUBATION, $M_n = 3.2 \times 10^5$ $M_w = 6.6 \times 10^5$ D.

C) LIGNIN SULFONATE FROM A GLUCOSE AND LIGNIN-SULFONATE CULTURE AFTER 29 DAYS OF INCUBATION, $M_n = M_w = 1.5 \times 10^6$ D.

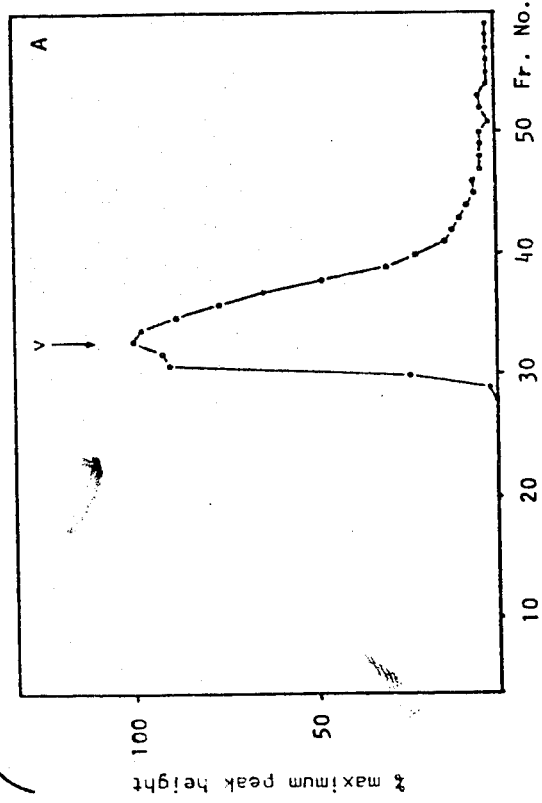

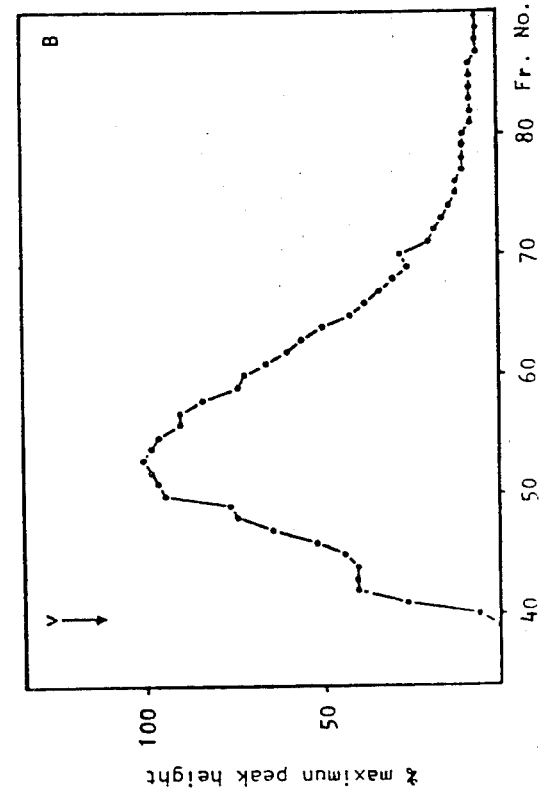

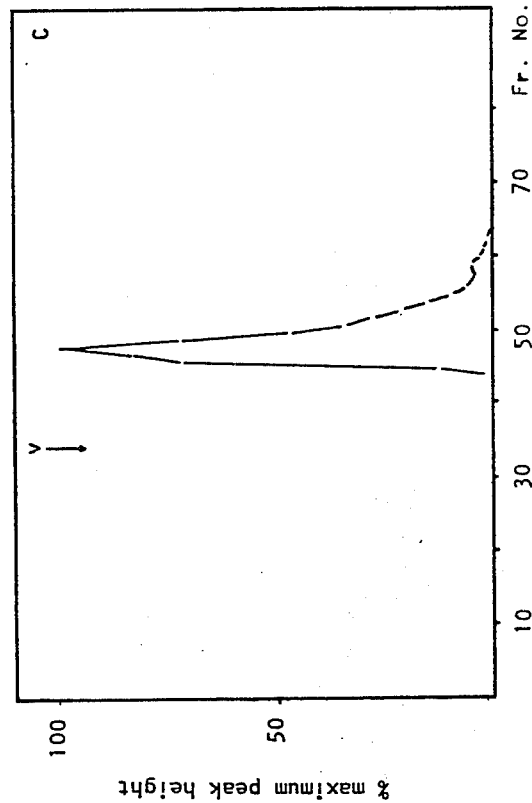

PROCESS FOR PRODUCING A BINDER FOR WOOD MATERIALS

The invention concerns a process for employing phenolic substances, especially lignin sulfonate to produce a binder for wood materials.

Almost 20% of the chemical pulp and dissolving pulp provided worldwide is produced by the sulfite process. The significance of this process continues to grow with the large-scale employment of modifiable magnesium bisulfite pulping. This emphasizes the importance of finding economical methods of exploiting sulfite spent liquors. Although there exists an especially wide range of uses for lignin sulfonates derived from these liquors, they are still not enough to fully utilize the 50 million tons per year left over from the production of pulp. Only 8-10% of the yield of lignin sulfonate is presently being economically employed, with the rest being dumped into rivers or burned.

Disposing of the spent liquors to minimize the pollution of rivers, however, presents problems. The 88% water they contain must first be evaporated. This requires a lot of energy (20-50% of the energy obtained by combustion) and the evaporated water will retain all the volatile components of the liquor, leaving the condensate with a high biochemical oxygen demand.

Quite aside from their environmental effects, however, both processes involve a huge waste of raw materials because the conventional sulfite process results in a loss of approximately 60% of the total amount of wood employed.

A process that would make rational use of the sulfite spent liquors would be highly desirable not only from the aspect of environmental protection but also from that of the optimum consumption of raw materials. A channel for research in lignin chemistry leading to the rational exploitation of the resulting sulfite spent liquors has been open for quite some time. The guiding principle of this research has been that any means of exploiting the liquors that results in values higher than the pure calorific value of the liquors is desirable.

One industry that has long been seeking means of employing sulfite spent liquors is the particleboard industry. Finding the proper binders for particleboards with particular properties for special applications is especially important. Particleboards manufactured in The Federal Republic of Germany for interior construction are bound almost exclusively with urea-formaldhyde (UF) resins, which are, however, moisture-resistant only under certain conditions. At temperatures above 50° C. such boards will not stand up to water. This low wet strength makes UF-bonded boards unsuited for exterior uses. Akaline-curing phenol-formaldehyde (PF) resins have been introduced since 1963. The drawbacks of this type of binding, which include long pressing times and unsatisfactory swelling, provide the motivation for seeking other binders which improved resistance to climatic demands.

Sulfite spent liquors have been employed along with diisocyanates and tannic resins as extenders with binders. Long pressing times and high pressing temperatures are the main disadvantages. Further research into the employment of lignin sulfonates in the adhesion process is known from Roffael in German Pat. No. 2 406 887. This made it possible to leave out 50% of the expensive phenol-formaldehyde resin, and substitute the cheaper sodium sulfite liquor without lowering the physical and chemical properties of the boards below the levels prescribed in the DIN standards for a bulk density of 0.7 $g/m^3$. The lignin sulfonate binder, however, still does not participate actively in the adhesion.

The purpose of the present invention is a process for the manufacture of phenolic binder comprising of sulfite spent liquors or the lignin sulfonate that they contain, as active binders for wood products.

This purpose is achieved in accordance with the invention by activating the phenolic substance with enzymes that employ a radical mechanism to oxidatively polymerize phenols, changing the substance into an active binder. The phenolic material treated with enzymes becomes an active binder itself and can be applied for example to particles of wood that are to be bonded together. This active binder can be used in the manufacture of particleboard for example. Such board can be compressed under very low pressures and stacked for curing at room temperature. Phenol-oxidizing enzymes securely bond the lignin sulfonate in the sulfite liquor to the wood by oxidative polymerization during this curing process.

The enzymes that employ a radical mechanism to oxidatively polymerize the phenols can be obtained from plants, fungi, or bacteria, especially from white-rot fungi. Such white-rot fungi include:

Polyporus sp.
Stereum sp.
Marasmius sp.
Fomes sp.
Pleurotus sp. and
Sporotrichum sp.

Some appropriate plants are
*Amoracia rusticana* and
*Rhus vernicifera*.

A broth of simple organic and inorganic nutrients for stimulating the production of enzymes can be employed. An extremely dilute phenol can be used for the inductor.

The invention will now be explained in detail. The basidiomycete Fomes annosus, like other white-rot fungi, releases phenol-oxidizing enzymes into a culture medium that contains lignin sulfonate and an additional source of carbon. Phenol-oxidizing enzymes shall be understood to mean $O_2$ acceptor:
  o-diphenoloxidase
  p-diphenoloxidase (laccase)
$H_2O_2$ acceptor:
  peroxidase.

Some especially appropriate enzymes are:

| E.C. No. | Systematic Name | Reaction | Specificity, etc |
|---|---|---|---|
| 1.10.3.1 | o-diphenol: oxygen oxidoreductase (polyphenoloxidase, phenolase, tyrosinase, catechol oxidase) | 2 o-diphenol + $O_2 \rightarrow$ 2 o-quinone + $2H_2O$ | Cu as central atom; monophenols also oxidized. |
| 1.10.3.2 | p-diphenol: oxygen oxidoreductase (laccase) | 2 p-diphenol + 0 $\rightarrow$ 2 p-quinone + $2H_2O$ | Cu as central atom; p-phenylene diamines are also oxidized |
| 1.11.1.7 | Donor: hydrogen peroxide oxidoreductase | donor + $H_2O_2$ = oxidized donor + $H_2O$. | hemoprotein |

| E.C. No. | Systematic Name | Reaction | Specificity, etc |
|---|---|---|---|
| | (perooxidase) | | |

The enzyme in the case of Fomes annosas is laccase (E.C. 1.10.3.2). This enzyme oxidizes phenols in accordance with the reaction

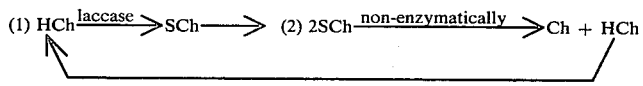

where
HCh=hydroquinone
SCh=semiquinone and
Ch=quinone.

The electron acceptor of this enzyme is the central atom $Cu^{2+}$. It regenerates by passing the electrons on to $O_2$. ($H_2O_2$ also functions as an acceptor with peroxidase.)

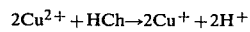

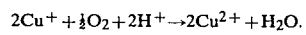

The enzyme also uses the same reaction to oxidize higher-molecular weight polyphenols (like lignins or lignin sulfonic acids). In this case, the mesomeric free radicals that occur in the first, enzymatically catalyzed stage will couple. This will very rapidly result in a high-molecular weight, amorphous dehydrogenation polymerizate. To illustrate this reaction, FIG. 1 shows the formation of lignin from monomerics by means of peroxidase.

Figure 2:
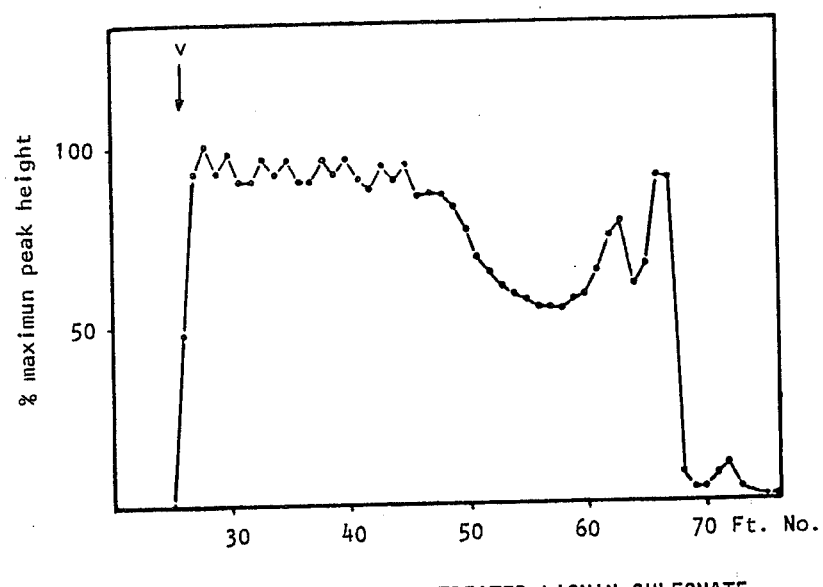
Figure 4:
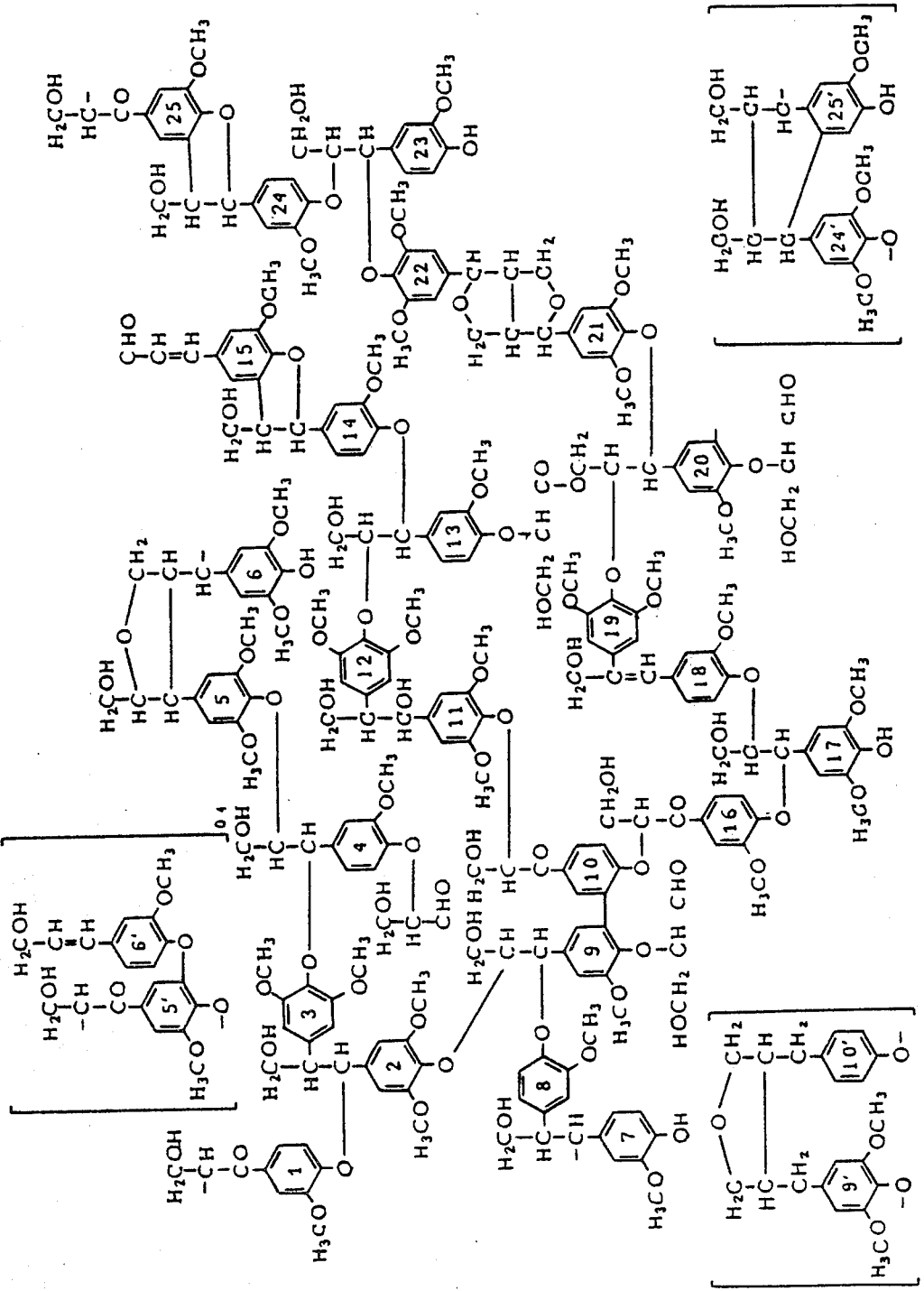

FIGS. 2 and 3 demonstrate that polyphenols of *higher* molecular weight are also oxidatively polymerized. FIG. 2 shows native lignin sulfonate with a broad distribution of molecular weight and a mean of 435 000. This is polymerized during 19 days culturing by Fomes annosus into a product with a molecular weight of $1.5 \times 10^6$ (FIG. 3). The same is true for other insoluble lignins. FIG. 4 shows the structure of such a lignin.

The binder produced in such a process is especially practical in the manufacture of wood products, particleboard in particular. The matte formed of wood particles can be lightly pressed at room temperature, which does, however, not exclude the use of the pressures normally employed in the particleboard industry, although they will not be necessary in most cases.

The binding of wooden chips that occurs in accordance with the reaction described above provides a number of advantages over the known method of manufacturing particleboard.

The sulfite spent liquor derived from waste, or the lignin sulfonate it contains, can be used to culture organisms for their enzymes as well as for the activated binder. This is a significant contribution toward deactivating the spent liquor problem. It also saves the expensive phenol resins and isocyanates.

Finally, the method in accordance with the invention uses much less energy than comparable methods of manufacturing particleboard, because the product can be both pressed and tempered at room temperature and with slight pressure. The boards are environmentally sound because they do not release formaldehyde. They do not contain enough alkali to produce rust stains around the nails used to fasten the boards, as occurs with products bound with phenol resin.

An example of one embodiment of the invention will now be described.

1. Obtaining the enzyme

The white-rot fungus Fomes annosus (ATCC 28222) was cultured axenically in 50 ml of liquid medium with the composition 2.5% lignin sulfonic acid
1.5% glucose
0.25% aspartic acid
0.7% $KH_2PO_4$
0.4% $KNO_3$
0.3% $Na_2HPO_4.2H_2O$
0.1% $MgSO_4.7H_2O$
0.1% NaCl in a 500-ml Erlenmeyer flask.

As trace elements serve Mn $Cl_2$, $ZnSO_4$, $CoCl_2$, $CuCl_2$, $FeCl_2$.

After 10 days of incubation at 24° C. in the dark, the laccase-inducing phenol 2,4-dihydroxybenzoic acid was added as a stock solution. The final concentration of the inductor was 2 mM. After 2 more days of incubation under the same external conditions, the mycelium mats were removed over No. 1575 Schleicher and Schüll filter paper in a water-jet vacuum and the mycel-free culture medium (=filtrate) desalinated by filtration over Sephadex $G_{25}$ and concentrated to 1/5 of its volume in a rotary evaporator at 25° C. The filtrate can also be desalinated and concentrated by diafiltration (Amicon DC 2, filter cutoff 10000). This medium contained 10 units/ml of laccase.

2. Producing the binder:

Various sulfite spent liquors (of varying cellulose plants) and pure sodium lignin sulfonate were slowly stirred into 1 ml of the enzyme solution produced as described above until the suspension reached the consistency of honey. The same liquor was employed as a control, mixed with demineralized water instead of the enzyme solution.

3. Binding wood particles meeting DIN specifications:

Pieces of wood conforming to the DIN specifications were uniformly coated on each side to be bonded with the various types of adhesive (approximately 1-mm thick) and pressed together at a pressure of 0.03 kg/cm². The adhesiveness (N/mm²) of the binder was then measured in a DIN device, with the following results:

| Adhesiveness of various sulfite spent liquors | |
|---|---|
| Liquor | Adhesiveness (N/mm²) |
| 1 | 0.1 |
| 2 | 0.04 |
| 3 | 0.29 |
| 4 | 0.1 |
| 5 | 0.15 |

Control tests without added enzyme yielded no adhesion.

It was shown that various types of adhesive of various provenance differ in adhesiveness. The best results were obtained with Sample 3, with an adhesiveness of 0.29 newtons per mm², demonstrating that particleboards with long-lasting adhesiveness can be attained.

We claim:

1. A process for producing an active binder for wood products from a phenolic compound having phenolic groups, including lignin sulfonate, comprising: treating said phenolic compound with enzymes to activate and oxidatively polymerize said phenolic compound by a radical mechanism to convert said phenolic compound into an active binder for wood products, permitting said active binder to bond wood products at predetermined temperature and predetermined applied pressure.

2. The process of claim 1, wherein said enzymes are selected as a member from the group consisting of plants, fungi, and bacteria.

3. The process of claim 1, wherein said enzymes are selected from a member of the group consisting of nutrient broth or plants, fungi, and bacteria.

4. The process of claim 3, wherein said broth of organic and inorganic nutrients includes means to stimulate the production of enzymes therein.

5. The process of claim 1, wherein said active binder is mixed with wood particles which are pressed at room temperature to form particleboard.

6. The process of claim 1, wherein said predetermined temperature is room temperature and said predetermined pressure is 0.03 Kg/cm².

* * * * *